US006838576B1

(12) United States Patent
Wicki et al.

(10) Patent No.: US 6,838,576 B1
(45) Date of Patent: Jan. 4, 2005

(54) PROCESS FOR PREPARING FUNCTIONAL GROUP-CONTAINING OLEFINIC COMPOUNDS

(75) Inventors: Markus A. Wicki, London (CA); Kent E. Nielsen, Dorchester (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/692,358

(22) Filed: Oct. 23, 2003

(51) Int. Cl.$^7$ .......................... C07C 67/00; C07C 29/00; C07C 27/00
(52) U.S. Cl. ...................... 560/210; 560/217; 568/850; 568/878
(58) Field of Search ................................ 560/210, 217; 568/850, 878

(56) References Cited

U.S. PATENT DOCUMENTS

| | | |
|---|---|---|
| 3,752,843 A | 8/1973 | Henrick |
| 3,783,135 A | 1/1974 | Henrick et al. |
| 3,805,607 A | 4/1974 | Heusser |
| 3,818,049 A | 6/1974 | Henrick et al. |
| 3,875,243 A | 4/1975 | Descoins et al. |
| 3,943,157 A | 3/1976 | Henrick et al. |
| 4,189,614 A | 2/1980 | Samain et al. |
| 4,912,253 A | 3/1990 | Fukumoto et al. |
| 4,973,765 A | 11/1990 | Mackenroth et al. |
| 5,089,659 A | 2/1992 | Brueckner et al. |
| 5,292,973 A | 3/1994 | Fukumoto et al. |
| 5,395,993 A | 3/1995 | Klein et al. |
| 5,481,040 A | 1/1996 | Fukumoto et al. |
| 5,599,848 A | 2/1997 | Klein et al. |
| 6,248,364 B1 | 6/2001 | Sengupta et al. |

FOREIGN PATENT DOCUMENTS

| | | |
|---|---|---|
| CZ | 233069 | 5/1983 |
| DE | 2355534 | 9/1975 |
| DE | 3829979 A1 | 3/1990 |
| EP | 0 038 052 B1 | 10/1981 |
| EP | 0 241 335 B1 | 10/1987 |
| EP | 0 569 805 B1 | 3/1997 |
| GB | 1299691 | 12/1972 |
| JP | 58177924 A | 10/1983 |
| JP | 62212347 A | 9/1987 |
| JP | 3240752 A | 10/1991 |
| JP | 1996506573 A | 7/1996 |
| RO | 64550 | 8/1978 |
| RO | 76824 | 8/1981 |
| RO | 84426 | 8/1984 |
| WO | WO 94/17662 | 8/1994 |
| WO | WO 99/56541 | 11/1999 |

OTHER PUBLICATIONS

Vincer et al., "Synthesis of Pheromones, III", *Acta Chimica Hungarica*, vol. 124, No. 5, pp. 737–748, (1987).

Kang et al., "Synthesis of (Z)–, and (E)–8–Dodecen–1–yl Acetate, The Sex Pheromone Of The Oriental Fruit Moth, Grapholitha Molesta By Stereochemical Control in Wittig Olefination" *Bull. Korean Chem. Soc.* vol. 7, No. 6, 1986, pp. 453–457.

Stowell, J.C., "A Short Synthesis Of The Sex Pheromone Of The Pink Bollworm Moth", *Journal of Organic Chemistry*, vol. 35, Jan. 1, 1970, pp. 244–245.

Babler, J. H., and Haack, R.A., "A Facile Stereoselective Route To The Sex Pheromone Of The Codling Moth Via Thermolysis Of An Allylic Sulfoxide", *The Journal of Organic Chemistry*, vol. 47, No. 24, Nov. 19, 1982, pp. 4801–4803.

Nicolaou, K. C. et al., "Total Synthesis Of the CP–Molecules (CP–263,114 and CP–225,917, Phomoidrides B and A). Racemic And Asymmetric Synthesis Of Bycyclo[4.3.1] Key Building Blocks", *The Journal of Organic Chemistry. Soc.*, Mar. 13, 2002, vol. 124, No. 10, pp. 2183–2189.

Organic Reactions, vol. 8, John Wiley & Sons, Inc., New York, (1954) pp. 252.

Silverstein, R. M., "Practical Use Of Pheromones And Other Behavior–Modifying Compounds: Overview", *Behavior–Modifying Chemicals For Insect Management*, Edited by Ridgway, Silverstein, and Inscoe, Marcel Dekker, Inc., New York and Basel, 1990, pp. 6.

Vig, O.P., Vig, A.K., Gauba, A.L. , and Gupta, K.C.; "A New Synthesis of trans–8–trans–10–dodecadien–1–ol", *Journal of The Indian Chemical Society*, vol. LII, Jun. 1975, pp. 541–542.

Kulkarni, et al., "Synthesis of Dienic Pheromones Of Codling Moth & Grape Vine Moth", *Indian Journal of Chemistry*, vol. 23B, Dec. 1984, pp. 1208–1210.

Naoshima, Y, et al., "A New Synthesis of (E,)–8–10–Dodecadien–1o1, Sex Pheromone Of Codling Moth", *Agricultural and Biological Chemistry*, May 1980, vol. 44(6), pp. 1419–1420.

(List continued on next page.)

Primary Examiner—Samuel Barts
Assistant Examiner—Sikarl A. Witherspoon
(74) Attorney, Agent, or Firm—Lisa P. Fulton

(57) ABSTRACT

A process for preparing functional group-containing olefinic compounds comprises the steps of (a) reacting at least one alkylidene phosphorane with at least one carbonyl-containing compound that comprises at least one group that is a leaving group, or that is capable of subsequent conversion to a leaving group, to form an olefinic compound that comprises at least one leaving group, the carbonyl-containing compound being selected from the group consisting of ketones and aldehydes; and (b) reacting the olefinic compound with at least one functional group-containing nucleophile to form a functional group-containing olefinic compound.

47 Claims, No Drawings

OTHER PUBLICATIONS

Ando, T.; et al., "Systematic Syntheses And Characterization Of Dodecadien–1–ols With Conjugated Double Bond, Lepidopterous Sex Pheromones", *Agricultural and Biological Chemistry*, Jan. 1985, vol. 49(1), pp. 141–148.

Descoins, C., and Hendrick, C. A., "Stereoselective Synthesis Of A Sex Attractant Of The Cooling Moth", *Tetrahedron Letters*, No. 30, Pergamon Press, 1972, pp. 2999–3002.

Bloch, R., and Abecassis, J., "A General And Stereoselective Synthesis Of (E,E)–Conjugated Dienes", *Tetrahedron Letters*, vol. 24, No. 12, Pergamon Press, 1983, pp. 1247–1250.

Pagni, R. M., and Watson, Jr., C. R., "The Reaction Of Phenalenone With Aluminum Hydrides", *Tetrahedron Letters*, vol. 29, Pergamon Press, 1974, pp. 3807–3810.

Du Penhoat, C. H., and Julia, M., "Synthesis With Sulfones XLIV. Stereoselective Preparation Of EE 1,3–Dienes By Elimination Of Benzenesulfinic Acid From E. Homoallyic Sulfones", *Tetrahedron Letters*, vol. 42, No. 17, Pergamon Press, 1986, pp. 4807–4816.

Bestman, H. J., Sub, J., and Vostrowsky, O., "Phermone XXVI. Synthesis Der Sexuallockstoffe (E)–7, (Z)–9–Dodecadienylacetat, (E)–9,11–Dodecadienylacetat Und (Z)–9,(E)–11–Tetradecadienylacetat", No. 25, *Tetrahedron Letters*, Pergamon Press, (1979), pp. 2467–2470.

Babler, J. H., and Coghlan, M. J.; "A Facile Method For Monoacetylation Of Symmetrical Diols: Application To The Total Synthesis Of Z–8–Dodecenyl Acetate, The Sex Attractant Of The Oriental Fruit Moth", Pergamon Press ltd., *Tetrahedron Letters*, No. 22, 1979, pp. 1971–1974.

Popovici, N., "Synthesis Of the Sex Pheromone Of the Codling Moth," *Revue Roumaine de Chemie*, 1997, vol. 42, No. 3, 1997, pp. 221–224.

8th International Congress of Pesticide Chemistry Options 2000, American Chemical Society, Washington, D.C., 1995, pp. 94.

Kukovinets, O.S. et al., "Ozonolysis Of Alkenes And Study Of Reactions Of Polyfunctional Compounds: LXII. New Synthetic Route To 7E,9Z–Dedecadien–1–yl Acetate, Pheromone Of The Leaf Roller Moth (*Lobesia botrana*)", Russian Journal of Organic Chemistry, vol. 36, No. 2, Feb. 2000, pp. 211–213.

Kukovinets, O.S., et al., "Alkene Ozonolysis And The Study Of Reactions Of Polyfunctional Compounds: LXI. New Synthetic Route To Bombycol, Pheromone Of Mulberry Silkworm", Russian Journal of Organic Chemistry, vol. 35, No. 8, Aug. 1999, pp. 1156–1159.

Odinokov, V. N., et al., "Insect Pheromones And Their Analogs, Lvii. Synthesis Of The Racemic Analog *Of The Sex Pheromone Of Pine Sawflies Of The Genera*" Chemistry of Natural Compounds (Translated from Russian), vol. 34, No. 1, Jan.–Feb. 1998, Plenum Publishing Corporation, pp. 96–98.

Kukovinets, O. S., et al., "Insect Pheromones And Their Analogs LIX. A New Method For the Synthesis Of Components Of The Sex Pheromones Of Insects Of the Genus Malocosoma", Chemistry of Natural Compounds, vol. 35, No. 3, 1999, pp. 358–360.

Gil, S., et al., "Sex Pheromone Of Chilo Suppressalis: Efficient Syntheses Of (z)–11–Hexadecenal, (z)–13–Octadecenal and (z)–9–Hexadecenal", Synthetic Communications, vol. 26, No. 12, 1996 pp. 2329–2340.

Dudkin, M. S., and Denisyuk, N.A., "Strucutre Of A Glucuronoxylan From Alfalfa Sterns", Chemistry of Natural Compounds Khimiya Prirodnykh Soedinenil, (Translated from Russian), vol. 25, No. 3, May–Jun. 1989, Plenum Publishing Corporation, pp. 276–278.

Deng et al., "Syntheses of Insect Pheromones By Phase Transfer Catalytic Wittig Reactions", *Chinese Science Bulletin*, Feb. 1989, vol. 34, No. 3, pp. 203–206.

Jiang et al., Huaxue Shiji, 1988, vol. 10, No. 3, pp. 131–132.

Popovici et al, "Exo– and Endohormones. VII[1] Synthesis of Z–11–Tetrahedron–1–OL Acetate By Phosphonium Ylide Condensation", *Revue Roumaine de Chimie*, 1983, vol. 28, No. 11–12, pp. 995–999.

Zhang et al., "Identification And Synthesis Of Female Sex Pheromone Of Oriental Beetle, Anomala Orientalis (Coleopters: Scarabaeidae)," Journal of Chemical Ecology, vol. 20, No. 9, 1994, pp. 2415–2427.

Kovalev, B. G. and Al'tmark, E. M., "The Unsymmetrical Extension Of The Chain Of Keto Aldehydes In The Wittig Reaction", Translated from Zhurnal Organicheskoi Khimii, vol. 8, No. 8, pp. 1582–1587, Aug. 1972, 1973. Consultants Bureau, a division of Plenum Publishing Corporation, New York, pp. 1616–1620.

PROCESS FOR PREPARING FUNCTIONAL GROUP-CONTAINING OLEFINIC COMPOUNDS

FIELD

This invention relates to a process for preparing functional group-containing olefinic compounds such as, for example, flavors, fragrances, and semiochemicals.

BACKGROUND

Insect pests such as, for example, leafrollers, tomato pinworms, oriental fruit moths, and codling moths can cause significant damage and economic loss in the production of tree fruits, vine and nut crops, and various other crops. In the past, such insect pests were typically controlled with pesticides such as, for example, organophosphate pesticides. Due to regulatory and environmental pressures, however, insect pest control is moving away from exclusive reliance on pesticides. As a result, alternative crop protection strategies such as insect mating disruption technology have steadily increased in general acceptance.

Insect mating disruption is an important component of the modern approach to pest regulation known as integrated pest management, which combines biological, cultural, physical, and chemical techniques to regulate pest populations while minimizing cost and environmental disturbances. The typical mating disruption technique confuses male insects with pheromones from the natural chemical blends of conspecific females. Sources of sex pheromone are placed in a crop or environment at concentrations sufficient to mask the presence of females. Decreasing or delaying the mating of the moths thus decreases the population of the next generation of larva, as well as the potential for future crop or environmental damage.

It is often difficult, however, to economically manufacture pheromone compounds for use in mating disruption techniques. Many methods for preparing pheromone compounds require complex multi-step sequences to arrive at the target compound (see, for example, Vincer et al., Acta Chim. Hung., 124, 737 (1987); WO 94/17662; and JP 3240752), or rely upon starting materials such as, for example, cis-alkenyl chlorides that are not readily available and necessitate preparation by multi-step processes (see, for example, EP 0 038 052 B1). Other methods yield only modest results such as, for example, less than 50% yield (see, for example Kang et al., Bull. Korean Chem. Soc. 7(6), 453 (1986)).

Also, in order for mating disruption techniques to be effective, synthetically prepared pheromones must closely mimic those naturally produced by insects. Natural insect pheromones are typically blends of stereoisomers. There is a very specific tuning of the isomeric blends in the pheromones released by insects. This tuning provides species specificity and proper biological effect. Minor alterations of the isomeric blends can inhibit the pheromonal effect. When preparing pheromone compounds, however, it is often difficult to control the stereoselectivity of the forming double bond to yield the desired stereoisomer.

SUMMARY

In view of the foregoing, we recognize that there is a need for a simplified synthetic route to pheromone compounds, which makes use of readily available and inexpensive raw materials, and that is easily scaleable. Furthermore, we recognize that it would be advantageous to have increased control over the stereoselectivity of the forming compounds.

Briefly, in the present invention provides a simple two-step process for preparing functional group-containing olefinic compounds such as, for example, flavors, fragrances, and semiochemicals. As used herein, "semiochemical" means a chemical that conveys a signal from one organism to another, for example, in such a way as to modify the behavior of the recipient organism (including, for example, allomones, kairomones, synomones, and pheromones, which can have, for example, arrestant, attractant, repellent, deterrent, or stimulant properties).

The process comprises the steps of:

(a) reacting (1) at least one alkylidene phosphorane comprising an alkylidene moiety and three other moieties bonded to its phosphorus atom, the alkylidene moiety optionally comprising one or more carbon to carbon double or triple bonds, with (2) at least one carbonyl-containing compound that comprises at least one group that is a leaving group, or that is capable of subsequent conversion to a leaving group, and that optionally comprises one or more isolated carbon to carbon double or triple bonds, to form an olefinic compound that comprises at least one leaving group, the carbonyl-containing compound being selected from the group consisting of ketones and aldehydes; and (b) reacting the olefinic compound with at least one functional group-containing nucleophile to form the corresponding functional group-containing olefinic compound.

The alkylidene phosphorane starting material for the process of the invention can be obtained from commercial suppliers, or can be easily prepared by reacting a phosphonium salt with a base.

The process of the invention therefore meets the need in the art for a scaleable and economic synthetic route to pheromone compounds, which makes use of readily available and inexpensive raw materials.

Furthermore, in preferred embodiments, it has been discovered that the stereoselectivity of the double bond forming step can be controlled by carefully choosing the substituents on the phosphorus of the alkylidene phosphorane starting compound. Surprisingly, when the substituents (that is, the three moieties other than the alkylidene moiety) are aryl groups or hetaryl groups, the process of the invention can provide a high yield of Z-configured functional group-containing olefins; when the substituents are alkyl groups or cycloalkyl groups, the process of the invention can provide a high yield of E-configured functional group-containing olefins. As used herein, the prefixes "Z" and "E" are used to designate the configuration of geometrical isomers in which there is a double bond between two carbon atoms. For example, when two atoms or radicals are positioned on one side of the carbon axis, the isomer is a Z-isomer (or cis-isomer); when they are on the opposite sides, the isomer is an E-isomer (or trans-isomer). Thus, the invention provides processes for preparing pheromone compounds that can provide a high yield of a desired isomer.

DETAILED DESCRIPTION

Alkylidene Phosphorane Starting Compounds

Alkylidene phosphorane starting compounds useful in carrying out the process of the invention include those that comprise an alkylidene moiety and three other moieties bonded to the phosphorus atom of the phosphorane. The alkylidene moiety can optionally comprise one or more carbon to carbon double or triple bonds. Preferably, the alkylidene moiety contains no carbon to carbon double or triple bonds, or contains one carbon to carbon double bond.

Alkylidene phosphorane compounds that are suitable for use in the invention include those that can be represented by the following general formula:

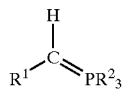

wherein $R^1$ is selected from the group consisting of hydrogen, alkyl groups, alkenyl groups, and alkynyl groups (preferably, $R^1$ has from about 1 to about 24 carbon atoms); and each $R^2$ is independently selected from the group consisting of aryl groups, hetaryl groups, alkyl groups, and cycloalkyl groups. As used herein, the terms "aryl groups," "hetaryl groups," and "cycloalkyl groups" include substituted aryls, substituted hetaryls, and substituted cycloalkyls, respectively; the term "alkyl groups" includes substituted or branched alkyls.

When Z-configured functional group-containing olefinic compounds are desired, $R^1$ is selected from the group consisting of hydrogen, alkyl groups, alkenyl groups, and alkynyl groups (preferably, $R^1$ is an alkyl group having from 1 to about 24 carbon atoms; more preferably, $R^1$ is selected from the group consisting of ethyl and propyl); and each $R^2$ is independently selected from the group consisting of aryl groups and hetaryl groups (preferably, each $R^2$ is an independently selected aryl group; more preferably, each $R^2$ is phenyl).

When E-configured functional group-containing olefinic compounds are desired, $R^1$ is selected from the group consisting of hydrogen, alkyl groups, alkenyl groups, and alkynyl groups (preferably, $R^1$ is an alkyl group or an alkenyl group having from 1 to about 24 carbon atoms; more preferably, $R^1$ is selected from the group consisting of propenyl and n-octyl); and each $R^2$ is independently selected from the group consisting of alkyl groups and cycloalkyl groups (preferably, each $R^2$ is an independently selected alkyl group; more preferably, each $R^2$ is selected from the group consisting of n-butyl and n-nonyl).

When approximately a 50:50 blend of Z-configured and E-configured functional group-containing olefinic compounds is desired, $R^1$ is preferably an alkyl group having from 1 to about 24 carbon atoms; one $R^2$ is an alkyl group; and the other two $R^2$ groups are independently selected aryl groups.

Other useful alkylidene phosphorane compounds include phosphine oxide anions and phosphonate anions that can be represented by the following general formula:

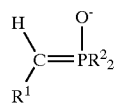

wherein $R^1$ is selected from the group consisting of hydrogen, alkyl groups, alkenyl groups, and alkynyl groups; and each $R^2$ is independently selected from the group consisting of aryl groups, hetaryl groups, alkyl groups, cycloalkyl groups, and alkoxy groups.

Representative examples of alkylidene phosphoranes that are useful starting materials include, for example, butylidenetriphenylphosphorane, propylidenetriphenylphosphorane, butenylidenetri(n-butyl)phosphorane, nonylidenetri(n-nonyl)phosphorane, 2-pentenylidenetri(n-butyl)phosphorane, propylidenetri(n-propyl)phosphorane, butylidenetri(n-butyl)phosphorane, pentylidene n-pentyldiphenylphosphorane, propylidenediphenylphosphine oxide anion, butenylidenediphenylphosphine oxide anion, nonylidenediphenylphosphine oxide anion, 2-pentenylidenediphenylphosphine oxide anion, butenylidene diethylphosphonate anion, nonylidene diethylphosphonate anion, and the like, and mixtures thereof.

Preferred alkylidene phosphorane starting compounds include, for example, butylidenetriphenylphosphorane, propylidenetriphenylphosphorane, butenylidenetri(n-butyl) phosphorane, nonylidenetri(n-nonyl)phosphorane, and the like, and mixtures thereof.

Useful alkylidene phosphorane starting compounds can be prepared, for example, by reacting a phosphonium salt, a phosphine oxide, or a phosphonate with a base.

Phosphonium salts that are useful for making the alkylidene phosphorane starting compounds of the invention include those that can be represented by the following general formula:

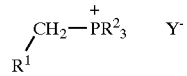

wherein $R^1$ is selected from the group consisting of hydrogen, alkyl groups, alkenyl groups, and alkynyl groups; each $R^2$ is independently selected from the group consisting of aryl groups, hetaryl groups, alkyl groups, and cycloalkyl groups; and $Y^-$ is selected from the group consisting of halides, aryl or alkyl sulfonates, and borates.

Preferably, $Y^-$ is a halide. More preferably, $Y^-$ is $Cl^-$ or $Br^-$. Most preferably, $Y^-$ is $Br^-$.

Representative examples of useful phosphonium salts include, for example, tetra(n-nonyl)phosphonium bromide, n-propyltriphenylphosphonium bromide, n-butyltriphenylphosphonium bromide, butenyltri(n-butyl) phosphonium bromide, di(n-pentyl)diphenylphosphonium bromide, tetra(n-propyl)phosphonium bromide, tetra(n-butyl)phosphonium bromide, 2-pentenyltri(n-butyl) phosphonium bromide, and the like, and mixtures thereof.

Preferred phosphonium salts include, for example, n-propyltriphenylphosphonium bromide, n-butyltriphenylphosphonium bromide, butenyltri(n-butyl) phosphonium bromide, tetra(n-nonyl)phosphonium bromide, and the like, and mixtures thereof.

Phosphine oxides and phosphonates that are useful for making the alkylidene phosphorane starting compounds of the invention include those that can be represented by the following general formula:

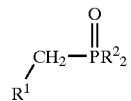

wherein $R^1$ is selected from the group consisting of hydrogen, alkyl groups, alkenyl groups, and alkynyl groups; and each $R^2$ is independently selected from the group consisting of aryl groups, hetaryl groups, alkyl groups, cycloalkyl groups, and alkoxy groups.

Useful bases include, for example, metal alkoxides, metal amides, organometallic bases, and the like, and mixtures thereof.

Preferred bases include potassium tert-butoxide, sodium hexamethyldisilazide, n-butyllithium, and the like, and mixtures thereof.

Preferably, the reaction of the phosphonium salt with the base is carried out in an inert atmosphere in the presence of an anhydrous solvent. Examples of useful anhydrous solvents include anhydrous acetonitrile, tetrahydrofuran, toluene, hexane, heptane, methyl tert-butyl ether, and the like, and mixtures thereof. Preferably, the reaction mixture is agitated. The reaction can be carried out at a temperature between about −100° C. and about 100° C. (preferably, between about 0° C. and 40° C.; more preferably, at room temperature).

Carbonyl-Containing Starting Compounds

Carbonyl-containing starting compounds useful in the process of the invention include those that comprise at least one group that is a leaving group, or that is capable of subsequent conversion to a leaving group, and optionally comprise one or more isolated carbon to carbon double or triple bonds. Such compounds can be selected from the group consisting of ketones and aldehydes.

As used herein, "leaving group" means a group that exits a molecule with an electron pair such that the molecule is capable of participating in a nucleophilic substitution reaction; a group "capable of subsequent conversion to a leaving group" means a group that can be readily converted into a leaving group (for example, a group that can be converted into a leaving group with one step such as, for example, a reduction step or an oxidation step).

Preferably, the group is a leaving group. Representative examples of suitable leaving groups include halogens, carboxylates (for example, acetates or propionates), sulfonates (for example, mesylate, tosylate, or brosylate), ammonium, oxonium, and the like.

As used herein, "isolated" carbon to carbon double or triple bonds means that the carbon to carbon double or triple bonds cannot be adjacent to the carbonyl moiety of the carbonyl-containing compound. Preferably, however, the carbonyl-containing compound contains no carbon to carbon double or triple bonds.

A class of preferred ketones and aldehydes can be represented by the following general formula:

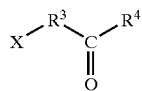

wherein X is a leaving group; $R^3$ is selected from the group consisting of alkylene, alkenylene, and alkynylene; and $R^4$ is selected from the group consisting of hydrogen, alkyl groups, alkenyl groups, and alkynyl groups.

Preferably, X is selected from the group consisting of Cl, Br, tosylate, mesylate, trifluoroacetate, and I (more preferably, X is Br); $R^3$ has from 1 to about 24 carbon atoms; and $R^4$ is selected from the group consisting of hydrogen and an alkyl group (more preferably, $R^4$ is hydrogen).

When Z-configured functional group-containing olefinic compounds are desired, $R^3$ is preferably selected from the group consisting of heptylene and decylene.

When E-configured functional group-containing olefinic compounds are desired, $R^3$ is preferably propylene or heptylene.

Representative examples of useful ketones and aldehydes include 5-chloropent-2-one, 5-bromopent-2-one, 4-bromobutan-1-al, 4-chlorobutan-1-al, 7-bromoheptan-1-al, 7-chloroheptan-1-al, 8-bromooctan-1-al, 8-chlorooctan-1-al, 9-bromononan-1-al, 9-chlorononan-1-al, 11-bromoundecan-1-al, 11-chloroundecan-1-al, 4-tosyloxybutan-1-al, 7-tosyloxyheptan-1-al, 8-tosyloxyoctan-1-al, 9-tosyloxynonan-1-al, 11-tosyloxyundecan-1-al, 4-mesyloxybutan-1-al, 7-mesyloxyheptan-1-al, 8-mesyloxyoctan-1-al, 9-mesyloxynonan-1-al, 11-mesyloxyundecan-1-al, and the like, and mixtures thereof.

Preferably, the carbonyl-containing compound is an aldehyde. Preferred aldehydes include, for example, 4-halobutan-1-al, 8-halooctan-1-al, 9-halononan-1-al, 11-haloundecan-1-al, and the like, and mixtures thereof. More preferred aldehydes include, for example, 4-chlorobutan-1-al, 8-bromooctan-1-al, 9-bromononan-1-al, 11-bromoundecan-1-al, and the like, and mixtures thereof.

When the desired end product of the process of the invention (that is, the functional group-containing olefinic compound) is a pheromone compound, the carbonyl moiety of the carbonyl-containing compound is bonded to the α-carbon atom of the longest chain of the carbonyl-containing compound, and the group that is a leaving group, or that is capable of subsequent conversion to a leaving group, is typically bonded to the ω-carbon atom of the longest chain.

Useful carbonyl-containing starting compounds can be prepared by oxidizing an alcohol having at least one group that is a leaving group, or that is capable of subsequent conversion to a leaving group, to form the corresponding carbonyl-containing compound. Oxidation reactions of this type are well known in the art. For example, it is well known that the dehydrogenation (that is, the removal of hydrogen by chemical means, which is a form of oxidation) of primary alcohols yields aldehydes.

Useful oxidizing agents include, for example, o-iodoxybenzoic acid (IBX), 2,2,6,6-tetramethyl-1-piperidinyloxy and derivatives (TEMPO), 1,1,1-tris (acetyloxy)-1,1-dihydro-1,2-benziodoxol-3-(1H)-one (Dess-Martin), dimethyl sulfoxide, sodium nitrite, sulfur trioxide/amine complex, and the like, and mixtures thereof.

Preferably, the reaction is carried out in the presence of a solvent such as an ether, halogenated solvent, or sulfoxide. Examples of useful solvents include, for example, dimethyl sulfoxide (DMSO), methylene chloride, methyl tert-butyl ether, and the like, and mixtures thereof. If desired, the reaction mixture can be agitated. The reaction can be carried out at a temperature between about −70° C. and about 60° C. (preferably, at room temperature).

Other examples of methods for preparing carbonyl-containing compounds include the reaction of alkyl halides with N-oxides of tertiary amines (J. Org. Chem., 35, 244 (1970)), the hydrogenation of acyl halides in the presence of Pd/BaSO$_4$ (Rosenmund reaction), or the reduction of carboxylic acids (Org. React., 8, 218 (1954)), acyl halides (Syn. Commun., 12, 839 (1982)), esters (Synthesis, 617, (1975)), and amides (Org. React., 8, 252 (1954)) with metal hydrides.

Functional Group-Containing Nucleophile Starting Compounds

The process of the invention includes the use of functional group-containing nucleophile starting materials. As used herein, the term "nucleophile" means an ion or molecule that can donate a pair of electrons to an atomic nucleus to form a covalent bond.

Useful functional group-containing nucleophiles include, for example, nucleophiles that contain an ester or alcohol (hydroxy) moiety, and nucleophiles that are capable of producing functional groups (such as, for example, aldehyde and ketone moieties) in situ. Representative examples of useful functional group-containing nucleophiles include, for example, carboxylates, sulfoxides, nitrogen oxides, hydroxides, and the like, and mixtures thereof. Specific examples of useful functional group-containing nucleophiles include, for example, sodium acetate, potassium acetate, trimethylamine N-oxide, pyridine-N-oxide, sodium hydroxide, potassium hydroxide, and the like, and mixtures thereof.

Preferably, the functional group-containing nucleophile is a carboxylate or a hydroxide. More preferably, it is an acetate or a hydroxide. Most preferably, it is a metal hydroxide (for example, sodium hydroxide or potassium hydroxide) or a metal acetate (for example, sodium acetate, or potassium acetate).

Preparation of Functional Group-Containing Olefinic Compound

The above-described alkylidene phosphorane and carbonyl-containing starting compounds can be brought together and allowed to react to form an olefinic intermediate compound comprising at least one leaving group ("olefinic intermediate compound"). The reaction is generally carried out under an inert gas atmosphere (that is, in the absence of oxygen), and under anhydrous conditions. Preferably, the reaction mixture is agitated.

A class of the olefinic intermediate compounds can be represented by the following general formula:

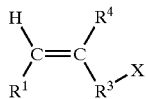

wherein X is a leaving group; $R^1$ is selected from the group consisting of hydrogen, alkyl groups, alkenyl groups, and alkynyl groups; $R^3$ is selected from the group consisting of alkylene, alkenylene, and alkynylene; and $R^4$ is selected from the group consisting of hydrogen, alkyl groups, alkenyl groups, and alkynyl groups.

If E-configured functional group-containing olefinic compounds are desired, the reaction mixture of the alkylidene phosphorane and carbonyl-containing starting compounds can be treated with a base before they are reacted with the above-described functional group-containing nucleophile starting compounds. Typically, when an alkylidene phosphorane compound with aryl or hetaryl substituents is used as a starting material in the process of the invention, the resulting functional group-containing olefinic compound has a predominantly Z-configuration. However, when the step of treating the reaction mixture with a base is added, the reaction can be steered to yield predominantly E-configured functional group-containing olefinic compounds. Bases that are useful for this step include organometallic bases such as, for example, phenyllithium.

The olefinic intermediate compounds can be reacted with the above-described functional group-containing nucleophile starting compounds to form the corresponding functional group-containing olefinic compounds. Preferably, the reaction is carried out in the presence of an aprotic dipolar solvent or an alcoholic solvent. Examples of useful solvents include, for example, ethanol, dimethyl formamide (DMF), N-methylpyrrolidinone (NMP), dimethyl sulfoxide (DMSO), and the like, and mixtures thereof. Preferably, the reaction mixture is agitated. The reaction can generally be carried out at a temperature between about 50° C. and about 200° C. (preferably, between about 80° C. and about 120° C.).

Alternatively, functional group-containing olefinic compounds can be prepared by a process comprising the steps of:
(a) reacting (1) at least one functional group-containing nucleophile with (2) at least one carbonyl-containing compound that comprises at least one group that is a leaving group, or that is capable of subsequent conversion to a leaving group, and that optionally comprises one or more isolated carbon to carbon double or triple bonds, to form the corresponding functional group-containing carbonyl-containing compound; the carbonyl-containing compound being selected from the group consisting of ketones and aldehydes; and
(b) reacting the functional group-containing carbonyl-containing compound with at least one alkylidene phosphorane comprising an alkylidene moiety and three other moieties bonded to its phosphorus atom, the alkylidene moiety to optionally comprising one or more carbon to carbon double or triple bonds, to form a functional group-containing olefinic compound.

If desired, olefinic esters prepared using the processes of the invention can be hydrolyzed to form the corresponding alcohols.

The invention thus provides processes for preparing functional group-containing olefinic compounds such as, for example, flavors, fragrances, and semiochemicals.

Representative flavor compounds that can be prepared using the process of the invention include, for example, Z-3-octen-1-ol (watermelon, cucumber flavor), Z-4-hepten-1-al (used in cream and butter), Z-3-hexenyl pyruvate (celery flavor), E-3-octen-2-ol (mushroom, tomato flavor), and E,E-2,4-hexadien-1-ol (pineapple flavor).

Representative fragrances that can be prepared using the process of the invention include, for example, Z-3-hexenyl acetate (sharp fruity green), Z-3-hexenyl methylbutyrate (green apples), E-2-heptenyl acetate (berry note), and E-2-octenyl butyrate.

Semiochemicals that can be prepared using the process of the invention can be useful, for example, in pheromones. Pheromone compounds are typically olefinic acetates, olefinic alcohols, olefinic aldehydes, or olefinic ketones.

Representative pheromone compounds that can be prepared using the process of the invention include, for example, 11-tetradecenal (for Eastern Spruce Budworm pheromone), 10-nonadecenal (for Yellow Headed Spruce Sawfly pheromone), 8,10-dodecadienol (for Codling Moth pheromone), 11-tetradecenol (for Tufted Apple Budmoth pheromone), 11-tetradecenyl acetate (for Tufted Apple Budmoth pheromone, Sparganothis Fruitworm pheromone, Leafroller pheromone, and Blackheaded Fireworm pheromone), 9-dodecenyl acetate (for Grape Berry Moth pheromone and Tea Tortrix pheromone), 4-tridecenyl acetate (for Tomato Pinworm pheromone), 7,11-hexadecadienyl acetate (for Pink Cotton Bullworm pheromone), 8-dodecenyl acetate (for Oriental Fruit Moth pheromone and Citrus Fruit Moth pheromone), and 3,13-octadecadienyl acetate (for Peach Tree Borer pheromone and Lesser Peach Tree Borer pheromone).

Preferred pheromone compounds include, for example, 8,10-dodecadienol, 11-tetradecenyl acetate, 4-tridecenyl acetate, and 8-dodecenyl acetate.

As described above, methods of the invention can be used to produce a high yield of a desired stereoisomer. Preferred stereoisomers include, for example, E,E-8,10-dodecadienol (for Codling Moth pheromone), Z-11-tetradecenyl acetate (for Leafroller pheromone), E-4-tridecenyl acetate (for Tomato Pinworm pheromone), and Z-8-dodecenyl acetate (for Oriental Fruit Moth pheromone).

Pheromone compounds prepared by the methods of the invention can be used in mating disruption products. For example, the pheromone compounds can be microencapsulated and used in sprayable compositions to control insect pest activity.

Preferred Embodiments of the Process

A preferred embodiment of the process of the invention provides a high yield of Z-isomers and comprises the steps of:

(a) reacting (1) a phosphorane compound selected from those represented by the following general formula:

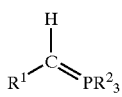

wherein:
R$^1$ is selected from the group consisting of hydrogen, alkyl groups, alkenyl groups, and alkynyl groups; and each R$^2$ is independently selected from the group consisting of aryl groups and hetaryl groups;
with (2) an aldehyde selected from those represented by the following general formula:

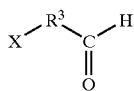

wherein:
X is a leaving group; and R$^3$ is selected from the group consisting of alkylene, alkenylene, and alkynylene; to form an olefinic compound represented by the following general formula:

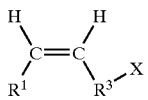

and
(b) reacting the olefinic compound with at least one carboxylate, sulfoxide, nitrogen oxide, or hydroxide to form the corresponding olefinic acetate, olefinic alcohol, olefinic aldehyde, or olefinic ketone.

Another preferred embodiment of the process of the invention provides a high yield of E-isomers and comprises the steps of:
(a) reacting (1) a phosphorane compound selected from those represented by the following general formula:

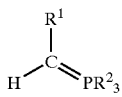

wherein:
R$^1$ is selected from the group consisting of hydrogen, alkyl groups, alkenyl groups, and alkynyl groups; and each R$^2$ is independently selected from the group consisting of alkyl groups and cycloalkyl groups;
with (2) an aldehyde selected from those represented by the following general formula:

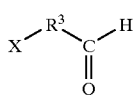

wherein:
X is a leaving group; and R$^3$ is selected from the group consisting of alkylene, alkenylene, and alkynylene; to form an olefinic compound represented by the following general formula:

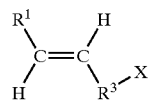

and
(b) reacting the olefinic compound with at least one carboxylate, sulfoxide, nitrogen oxide, or hydroxide to form the corresponding olefinic acetate, olefinic alcohol, olefinic aldehyde, or olefinic ketone.

EXAMPLES

Objects and advantages of this invention are further illustrated by the following examples, but the particular materials and amounts thereof recited in these examples, as well as other conditions and details, should not be construed to unduly limit this invention.

Preparation of Phosphonium Salts (Preparation of Tetra(n-propyl)phosphonium bromide)

In a 250 mL round bottom flask, n-propyl bromide (21.1 g, 171.5 mmol) (available from Sigma-Aldrich Canada) was dissolved in anhydrous acetonitrile (100 mL) under Ar-atmosphere, and tripropylphosphine (25 g, 156.0 mmol) (available from Sigma-Aldrich Canada) was added. The reaction mixture was heated at gentle reflux for 35 hrs. After cooling to room temperature, the solvent was removed under reduced pressure. The solid residue was suspended in toluene (50 mL) and the solvent was removed under reduced pressure. This process was repeated once. The solid residue was suspended in hexane (100 mL), filtered, washed with hexane (3×50 mL), and air-dried. The desired tetra (n-propyl)phosphonium bromide was obtained as colourless crystals (42.5 g, 96%).

Oxidation Protocol (Preparation of 8-bromooctan-1-al)

In a 250 mL round bottom flask, 8-bromooctan-1-ol (4.0 g, 19.1 mmol) (available from Sigma-Aldrich Canada) was dissolved in CH$_2$Cl$_2$ (40 mL) at room temperature. 2,2,6,6-Tetramethyl-1-piperidinyloxy free radical (TEMPO) (24.6 mg, 0.16 mmol) (available from Sigma-Aldrich Canada) was added to produce a red-coloured solution. A premix of NaOCl (5.25%, 36.7 g, 25.9 mmol) and saturated NaHCO$_3$ (25.9 mL) was added. The reaction mixture was vigorously stirred for 45 min. at room temperature. The progress of the conversion was monitored by gas chromatography-mass spectrometry (GC-MS) (Varian Saturn 2000 GC-MS). Additional NaOCl was added until complete conversion was obtained. Saturated Na$_2$SO$_3$ (20 mL) was added. The aqueous phase was separated and extracted with CH$_2$Cl$_2$ (2×20 mL). The resulting organic phase was washed with water (20 mL), and dried (Na$_2$SO$_4$). Evaporation of the solvent from the organic phase yielded the 8-bromooctan-1-al as an orange liquid (3.82 g, 96%).

Example 1

Preparation of Z/E-8-Dodecenyl Acetate
(Pheromone of the Oriental Fruit Moth)

To a colourless suspension of n-butyltriphenylphosphonium bromide (1.75 g, 4.39 mmol) (prepared essentially according to the Preparation of Phosphonium Salts, except that n-butyl bromide and triphenylphosphine were used as the reactants, and anhydrous toluene was used as the reaction solvent; also available from Sigma-Aldrich Canada) in toluene (20 mL) in a 50 mL round bottom flask was added potassium tert-butoxide (544 mg, 4.85 mmol) at room temperature under Ar-atmosphere. The suspension turned intensely orange-red in colour. The mixture was stirred at room temperature for 1 hour, after which time the colour had not changed. 8-Bromooctan-1-al (1.37 g, 6.61 mmol) (prepared essentially as described in the Oxidation Protocol) was added dropwise via syringe. The colour changed to light yellow. A weak exotherm was observed. The reaction mixture was stirred at room temperature for 30 min. Saturated aqueous $NH_4Cl$ (10 mL) and water (10 mL) were added. The aqueous phase was extracted with hexane (2×20 mL). The resulting organic phase was washed with $CH_3OH:H_2O$ (1:1) (3×15 mL) and brine (20 mL), and dried ($Na_2SO_4$). Evaporation of the solvent from the organic phase gave an orange liquid (2.29 g), which was purified by flash chromatography on $SiO_2$ (ethyl acetate:hexane (1:9)) to yield Z/E-8-dodecenyl bromide as a colourless liquid (1.01 mg, 93%).

Z/E-8-dodecenyl bromide (520 mg, 2.2 mmol), prepared as described above, was weighed into a 50 mL round bottom flask with a magnetic stir bar. Sodium acetate (540 mg, 6.6 mmol), freshly fused, was added in a single portion, followed by dimethyl formamide (5 mL). The flask was equipped with a condenser and was placed in a preheated oil bath (55° C.). The oil bath was further heated to 110° C. over 3 hours. The progress of the reaction was monitored by thin layer chromatography (TLC) using hexane:ethyl acetate in a ratio of 9:1 as the eluant. After 5 hours the reaction mixture was removed from the heat and allowed to cool to ambient temperature. Water (10 mL) was added to dilute the reaction mixture, and the resulting aqueous phase was extracted with hexane (3×15 mL). The combined hexane extracts were washed with water (2×10 mL) and brine (10 mL). The resulting organic phase was dried over $Na_2SO_4$, filtered, and the solvent evaporated under reduced pressure to yield the Z/E-8-dodecenyl acetate product as a clear liquid (360 mg, 73%). The Z/E ratio was determined to be 92:8 by gas chromatography (GC) using a DB-XLB column.

Example 2

Preparation of Z/Z-11-Tetradecenyl Acetate (Pheromone of the Oblique-band d L afroller)

To a colourless suspension of n-propyltriphenylphosphonium bromide (1.41 g, 3.6 mmol) in toluene (20 mL) (prepared essentially according to the Preparation of Phosphonium Salts, except that n-propyl bromide and triphenylphosphine were used as the reactants, and anhydrous toluene was used as the reaction solvent; also available from Sigma-Aldrich Canada) in a 50 mL round bottom flask was added potassium tert-butoxide (451 mg, 4.0 mmol) at room temperature under Ar-atmosphere. The suspension turned intensely red in colour. The mixture was stirred at room temperature for 1 hour, after which time the colour had not changed. 11-Bromoundecan-1-al (1.0 g, 4.0 mmol) (prepared essentially according to the Oxidation Protocol, but with 11-bromoundecan-1-ol as the starting material) was added dropwise via syringe. The colour changed to light yellow. A weak exotherm was observed. The reaction mixture was stirred at room temperature for 30 min. Saturated aqueous $NH_4Cl$ (10 mL) and water (10 mL) were added. The aqueous phase was extracted with hexane (2×20 mL). The resulting organic phase was washed with $CH_3OH:H_2O$ (1:1) (3×15 mL) and brine (20 mL), and dried ($Na_2SO_4$) Evaporation of the solvent from the organic phase gave a yellow liquid (2.13 g), which was purified by flash chromatography on $SiO_2$ (ethyl acetate:hexane (1:9)) to yield Z/E-11-tetradecenyl bromide as a colourless liquid (864 mg, 86%).

To a solution of Z/E-11-tetradecenyl bromide (466 mg, 1.7 mmol) in a 25 mL round bottom flask, prepared as described above, in dimethyl formamide (3 mL) was added fused sodium acetate (415 mg, 5.1 mmol), and the mixture was heated to 90–120° C. for 24 hrs. After cooling to room temperature, water (20 mL) was added and the mixture was extracted with ethyl acetate (3×20 mL). The resulting organic phase was washed with water (2×20 mL) and brine (20 mL), and dried ($Na_2SO_4$). Evaporation of the solvent yielded a brownish liquid (377 mg), which was purified by flash chromatography on $SiO_2$ (ethyl acetate:hexane (1:9)) to yield the Z/E-11-tetradecenyl acetate product as a colourless liquid (283 mg, 66%). The Z/E ratio was determined to be 91:9 by GC using a DB-Wax column.

Example 3

Preparation of 8,10-Dodecadienol (Pheromone of the Codling Moth)

To a colourless suspension of butenyltri(n-butyl)phosphonium bromide (1.48 g, 4.38 mmol) (prepared essentially according to the Preparation of Phosphonium Salts, except that butenyl bromide and tri(n-butyl)phosphine were used as the reactants) in toluene (20 mL) in a 50 mL round bottom flask was added n-butyllithium (2.5 M in hexanes, 1.95 mL, 4.88 mmol) at room temperature under Ar-atmosphere. The resulting yellow suspension was stirred for 1 hour at room temperature. 8-Bromooctan-1-al (1.0 g, 4.83 mmol) (prepared essentially as described in the Oxidation Protocol) was added dropwise via syringe. A weak exotherm was observed. The reaction mixture was stirred at room temperature for 30 min. Saturated aqueous $NH_4Cl$ (10 mL) and water (10 mL) were added. The aqueous phase was separated and extracted with heptane (2×20 mL). The resulting organic phase was washed with water (2×20 mL) and brine (20 mL), and dried ($Na_2SO_4$). Evaporation of the solvent from the organic phase gave a yellow liquid (1.45 g), which was purified by flash chromatography on $SiO_2$ (heptane) to yield 8,10-dodecadienyl bromide as a colourless liquid (736 mg, 68%). Quantitative $^{13}C$-NMR (nuclear magnetic resonance) analysis (using a Varian Inova 600 model) showed that the 8,10-dodecadienyl bromide product consisted of a mixture of all four possible stereoisomers in the following relative amounts:
E8,E10-isomer: 67%
Z8,E10-isomer: 16%
E8,Z10-isomer: 14%
Z8,Z10-isomer: 3%

8,10-dodecadienyl bromide (1.0 g, 4.08 mmol), prepared as described above, was dissolved in N-methylpyrrolidinone (0.96 mL) under Ar-atmosphere, and 50% NaOH (0.22 mL, 4.18 mmol) was added via syringe. The reaction mixture was heated to 95° C. for 4 hrs. A colourless precipitate was observed. After cooling to room temperature, water (10 mL) was added and the resulting mixture was extracted with heptane (3×6 mL). The resulting organic phase was washed with water (10 mL) and dried ($Na_2SO_4$). Evaporation of the solvent from the organic phase gave the 8,10-dodecadienol product as a yellow liquid (487 mg, 66%).

Example 4

Preparation of E/Z-8-Dodecenyl Acetate (Pheromone of the Citrus Fruit Moth)

To a colourless solution of tetra(n-butyl)phosphonium chloride (Cyphos™ 443T (available from Cytec Canada Inc., Niagara Falls, Ontario) 50% in toluene, 2.59 g, 4.38 mmol) in a 50 mL round bottom flask were added toluene (18.5 mL) and sodium hexamethyldisilazide (888 mg, 4.84 mmol) at room temperature under Ar-atmosphere. The resulting yellow suspension was stirred for 1 hour at room temperature. 8-Bromooctan-1-al (1.0 g, 4.83 mmol) (prepared essentially as described in the Oxidation Protocol) was added dropwise via syringe. A weak exotherm was observed. The reaction mixture was stirred at room temperature for 30 min. Saturated aqueous $NH_4Cl$ (10 mL) and water (10 mL) were added. The aqueous phase was separated and extracted with heptane (2×20 mL). The resulting organic phase was washed with water (25 mL) and brine (25 mL), and dried ($Na_2SO_4$). Evaporation of the solvent from the organic phase gave a yellow liquid (1.88 g), which was purified by flash chromatography on $SiO_2$ (heptane) to, yield E/Z-8-dodecenyl bromide as a colourless liquid (621 mg, 57%). GC analysis (Varian 3600 GC) determined an EZ/Z-ratio of 89:11.

The E/Z-8-dodecenyl bromide is converted to E/Z-8-dodecenyl acetate essentially as Z/E-8-dodecenyl bromide was converted to Z/E-8-dodecenyl acetate in Example 1.

Example 5

Preparation of E/Z-11-Tetradecenyl Acetate (Pheromone of the Sparganothis Fruitworm Pheromone)

To a colourless partial solution of tetra(n-propyl) phosphonium bromide (1.04 g, 3.65 mmol) (prepared essentially according to the Preparation of Phosphonium Salts) in toluene (20 mL) in a 50 mL round bottom flask was added sodium hexamethyldisilazide (738 mg, 4.02 mmol) at room temperature under Ar-atmosphere. The yellowish solution was stirred for 1 hour at room temperature. Freshly prepared 11-bromoundecan-1-al (1.0 g, 4.01 mmol) (prepared essentially according to the Oxidation Protocol, but with 11-bromoundecan-1-ol as the starting material) was added dropwise via syringe. A weak exotherm was observed. The reaction mixture was stirred at room temperature for 30 min. Saturated aqueous $NH_4Cl$ (10 mL) and water (10 mL) were added. The aqueous phase was separated and extracted with heptane (2×20 mL). The resulting organic phase was washed with water (25 mL) and brine (25 mL), and dried ($Na_2SO_4$). Evaporation of the solvent from the organic phase gave a yellow liquid (1.39 g), which was purified by flash chromatography on $SiO_2$ (heptane) to yield E/Z-11-tetradecenyl bromide as a colourless liquid (582 mg, 58%). GC analysis (Varian 3600 GC) determined an E/Z-ratio of 88:12.

The E/Z-11-tetradecenyl bromide is converted to E/Z-11-tetradecenyl acetate essentially as Z/E-11-tetradecenyl bromide was converted to Z/Z-11-tetradecenyl acetate in Example 2.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A process for preparing functional group-containing olefinic compounds comprising the steps of:
   (a) reacting (1) at least one alkylidene phosphorane comprising an alkylidene moiety and three other moieties bonded to its phosphorus atom, said alkylidene moiety optionally comprising one or more carbon to carbon double or triple bonds, with (2) at least one carbonyl-containing compound that comprises at least one group that is a leaving group, or that is capable of subsequent conversion to a leaving group, and that optionally comprises one or more isolated carbon to carbon double or triple bonds, to form an olefinic compound that comprises at least one leaving group, said carbonyl-containing compound being selected from the group consisting of ketones and aldehydes; and
   (b) reacting said olefinic compound with at least one functional group-containing nucleophile to form the corresponding functional group-containing olefinic compound.

2. The process of claim 1 further comprising the step of reacting a phosphonium salt, a phosphine oxide, or a phosphonate with a base to form said alkylidene phosphorane.

3. The process of claim 1 further comprising the step of oxidizing an alcohol having at least one group that is a leaving group, or that is capable of subsequent conversion to a leaving group, to form said carbonyl-containing compound.

4. The process of claim 1 wherein said functional group-containing olefinic compound is an olefinic ester, and further comprising the step of hydrolyzing said functional group-containing ester to form the corresponding alcohol.

5. The process of claim 1 wherein said alkylidene moiety of said alkylidene phosphorane contains no carbon to carbon double or triple bonds.

6. The process of claim 1 wherein said alkylidene moiety of said alkylidene phosphorane contains one carbon to carbon double bond.

7. The process of claim 1 wherein said three other moieties of said alkylidene phosphorane are independently selected from the group consisting of aryl and hetaryl.

8. The process of claim 1 wherein said three other moieties of said alkylidene phosphorane are independently selected from the group consisting of alkyl and cycloalkyl.

9. The process of claim 1 wherein one moiety of said three other moieties of said alkylidene phosphorane is an oxy anion, and the other two moieties of said three other moieties of said alkylidene phosphorane are independently selected from the group consisting of alkyl, cycloalkyl, aryl, hetaryl, and alkoxy.

10. The process of claim 1 wherein said carbonyl-containing compound contains no carbon to carbon double or triple bonds.

11. The process of claim 1 wherein said carbonyl-containing compound is an aldehyde.

12. The process of claim 11 wherein said aldehyde is selected from the group consisting of 4-halobutan-1-al, 8-halooctan-1-al, 9-halononan-1-al, and 11-haloundecan-1-al.

13. The process of claim 12 wherein said aldehyde is selected from the group consisting of 4-chlorobutan-1-al, 8-bromooctan-1-al, 9-bromononan-1-al, and 11-bromoundecan-1-al.

14. The process of claim 1 wherein the carbonyl moiety of said carbonyl-containing compound is bonded to the α-carbon atom of the longest chain of said carbonyl-containing compound, and said group that is a leaving group, or that is capable of subsequent conversion to a leaving group, is bonded to the ω-carbon atom of said longest chain.

15. The process of claim 1 wherein said group of said carbonyl-containing compound is a leaving group.

16. The process of claim 15 wherein said leaving group is selected from the group consisting of halogens, carboxylates, sulfonates, ammonium, and oxonium.

17. The process of claim 1 wherein said functional group-containing nucleophile is selected from the group consisting of carboxylates, sulfoxides, nitrogen oxides, hydroxides, and mixtures thereof.

18. The process of claim 17 wherein said functional group-containing nucleophile is selected from the group consisting of carboxylates and hydroxides.

19. The process of claim 18 wherein said carboxylates are acetates.

20. The process of claim 19 wherein said functional group-containing nucleophile is selected from the group consisting of metal hydroxides and metal acetates.

21. A process for preparing pheromone compounds comprising the steps of:
   (a) reacting (1) a phosphorane compound selected from those represented by the following general formula:

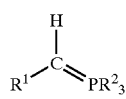

wherein:
   $R^1$ is selected from the group consisting of hydrogen, alkyl groups, alkenyl groups, and alkynyl groups; and
   each $R^2$ is independently selected from the group consisting of aryl groups and hetaryl groups;
with (2) an aldehyde selected from those represented by the following general formula:

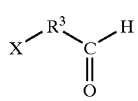

wherein:
   X is a leaving group; and $R^3$ is selected from the group consisting of alkylene, alkenylene, and alkynylene;
to form an olefinic compound represented by the following general formula:

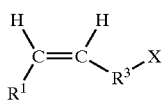

and
   (b) reacting said olefinic compound with at least one carboxylate, sulfoxide, nitrogen oxide, or hydroxide to form the corresponding olefinic acetate, olefinic alcohol, olefinic aldehyde, or olefinic ketone.

22. A process for preparing pheromone compounds comprising the steps of:
   (a) reacting (1) a phosphorane compound selected from those represented by the following general formula:

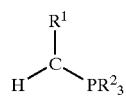

wherein:
   $R^1$ is selected from the group consisting of hydrogen, alkyl groups, alkenyl groups, and alkynyl groups; and
   each $R^2$ is independently selected from the group consisting of alkyl groups and cycloalkyl groups;
with (2) an aldehyde selected from those represented by the following general formula:

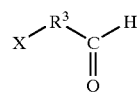

wherein:
   X is a leaving group; $R^3$ is selected from the group consisting of alkylene, alkenylene, and alkynylene;
to form an olefinic compound represented by the following general formula:

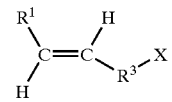

and
   (b) reacting said olefinic compound with at least one carboxylate, sulfoxide, nitrogen oxide, or hydroxide to form the corresponding olefinic acetate, olefinic alcohol, olefinic aldehyde, or olefinic ketone.

23. The process of claim 21 further comprising the step of reacting a phosphonium salt represented by the following general formula:

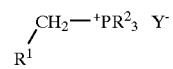

wherein:
   $R^1$ is selected from the group consisting of hydrogen, alkyl groups, alkenyl groups, and alkynyl groups; each $R^2$ is an independently selected aryl or hetaryl group; and $Y^-$ is selected from the group consisting of halides, aryl or alkyl sulfonates, and borates;
with a base to form said phosphorane compound.

24. The process of claim 22 further comprising the step of reacting a phosphonium salt represented by the following general formula:

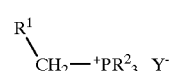

wherein:
   $R^1$ is selected from the group consisting of hydrogen, alkyl groups, alkenyl groups, and alkynyl groups; each $R^2$ is an independently selected alkyl or cycloalkyl group; and $Y^-$ is selected from the group consisting of halides, aryl or alkyl sulfonates, and borates;
with a base to form said phosphorane compound.

25. The process of claim 21 further comprising the step of oxidizing an alcohol represented by the following general formula:

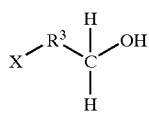

wherein:

X is a leaving group; and $R^3$ is selected from the group consisting of alkylene, alkenylene, and alkynylene; to form said aldehyde.

26. The process of claim 22 further comprising the step of oxidizing an alcohol represented by the following general formula:

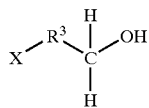

wherein:

X is a leaving group; and $R^3$ is selected from the group consisting of alkylene, alkenylene, and alkynylene; to form said aldehyde.

27. The process of claim 21 wherein said $R^1$ has from 1 to about 24 carbon atoms.

28. The process of claim 27 wherein said $R^1$ is an alkyl group.

29. The process of claim 28 wherein said $R^1$ is selected from the group consisting of ethyl and propyl.

30. The process of claim 22 wherein said $R^1$ has from 1 to about 24 carbon atoms.

31. The process of claim 30 wherein said $R^1$ is an alkyl group or an alkenyl group.

32. The process of claim 31 wherein said $R^1$ is selected from the group consisting of propenyl and n-octyl.

33. The process of claim 21 wherein each said $R^2$ is phenyl.

34. The process of claim 22 wherein each said $R^2$ is selected from the group consisting of n-butyl and n-nonyl.

35. The process of claim 21 wherein said $R^3$ has from 1 to about 24 carbon atoms.

36. The process of claim 35 wherein said $R^3$ is selected from the group consisting of heptylene and decylene.

37. The process of claim 22 wherein said $R^3$ has from 1 to about 24 carbon atoms.

38. The process of claim 37 wherein said $R^3$ is propylene or heptylene.

39. The process of claim 21 wherein said X is selected from the group consisting of Cl, Br, tosylate, mesylate, trifluoroacetate, and I.

40. The process of claim 39 wherein said X is Cl or Br.

41. The process of claim 22 wherein said X is selected from the group consisting of Cl, Br, tosylate, mesylate, trifluoroacetate, and I.

42. The process of claim 41 wherein said X is Cl or Br.

43. A process for preparing functional group-containing olefinic compounds comprising the steps of:

(a) reacting (1) at least one functional group-containing nucleophile with (2) at least one carbonyl-containing compound that comprises at least one group that is a leaving group, or that is capable of subsequent conversion to a leaving group, and that optionally comprises one or more isolated carbon to carbon double or triple bonds, to form the corresponding functional group-containing carbonyl-containing compound, said carbonyl-containing compound being selected from the group consisting of ketones and aldehydes; and (b) reacting said functional group-containing carbonyl-containing compound with at least one alkylidene phosphorane comprising an alkylidene moiety and three other moieties bonded to its phosphorus atom, said alkylidene moiety optionally comprising one or more carbon to carbon double or triple bonds, to form a functional group-containing olefinic compound.

44. A process for preparing 8-dodecenyl acetate comprising the steps of:

(a) reacting butylidenetriphenylphosphorane with 8-bromooctan-1-al to form 8-dodecenyl bromide; and (b) reacting said 8-dodecenyl bromide with sodium acetate to form 8-dodecenyl acetate.

45. A process for preparing 11-tetradecenyl acetate comprising the steps of:

(a) reacting propylidenetriphenylphosphorane with 11-bromoundecan-1-al to form 11-tetradecenyl bromide; and (b) reacting said 11-tetradecenyl bromide with sodium acetate to form 11-tetradecenyl acetate.

46. A process for preparing 8,10-dodecadienol comprising the steps of:

(a) reacting butenylidenetri(n-butyl)phosphorane with 8-bromooctan-1-al to form 8,10-dodecadienyl bromide;

(b) reacting said 8,10-dodecadienyl bromide with sodium acetate to form 8,10-dodecadienyl acetate; and (c) hydrolyzing said acetate to form 8,10-dodecadienol.

47. A process for preparing 8,10-dodecadienol comprising the steps of:

(a) reacting butenylidenetri(n-butyl)phosphorane with 8-bromooctan-1-al to form 8,10-dodecadienyl bromide;

(b) reacting said 8,10-dodecadienyl bromide with sodium hydroxide to form the 8,10-dodecadienol.

* * * * *

UNITED STATES PATENT AND TRADEMARK OFFICE
CERTIFICATE OF CORRECTION

PATENT NO. : 6,838,576 B1
DATED : January 4, 2005
INVENTOR(S) : Wicki, Markus A.

It is certified that error appears in the above-identified patent and that said Letters Patent is hereby corrected as shown below:

Title page,
Item [56], References Cited, OTHER PUBLICATIONS,
"Kulkarni," reference, delete "Coding" and insert -- Codling -- therefor.
"Du Penhoat," reference, delete "Homoallyic" and insert -- Homallylic -- therefor.
"Bestman" reference, delete "Bestman" and insert -- Bestmann -- therefor; delete "Phermone XXVI. Synthesis" and insert -- Phermone XXVI. Synthese -- therefor; delete "No. 25" and insert -- No. 26 -- .
"Popovici," reference, delete "Synthesis" and insert -- Syntheses -- .
"Kukovinets," reference, delete "Dedecadien" and insert -- Dodecadien -- therefor.
"Dudkin," reference, delete "Strucutre" and insert -- Structure -- therefor; delete "Sterns" and insert -- Stems -- ; delete "Soedinenil" and insert -- Soedinenii -- therefor.
"Deng" reference, delete "Reactions" and insert -- Reaction -- therefor.
"Popovici" reference, delete "Tetrahedron" and insert -- Tetradecen -- therefor.
"Kovalev," reference, after "1973", delete "." and insert -- , -- therefor.

Column 8,
Line 8, after "moiety" delete "to".

Column 13,
Line 17, delete "EZ/Z" and insert -- E/Z -- therefor.

Column 15,
Lines 61-65, delete " 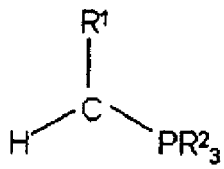 "and insert -- 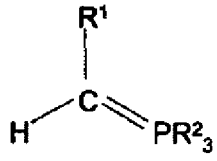 --, therefor.

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,838,576 B1
DATED : January 4, 2005
INVENTOR(S) : Wicki, Markus A.

It is certified that error appears in the above-identified patent and that said Letters Patent is hereby corrected as shown below:

Column 11,
Line 40, delete "Z/Z" and insert -- Z/E -- therefor.
Line 63, after "($Na_2SO_4$)" insert -- . -- therefor.

Signed and Sealed this

Twenty-third Day of August, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,838,576 B1 |
| APPLICATION NO. | : 10/692358 |
| DATED | : January 4, 2005 |
| INVENTOR(S) | : Markus A. Wicki |

It is certified that error appears in the above-identified patent and that said Letters Patent is hereby corrected as shown below:

Column 11,
Line 41, delete "(Pheromone of the Oblique-band d L afroller)" and insert
-- (Pheromone of the Oblique-banded Leafroller) --.

Signed and Sealed this

Sixteenth Day of October, 2007

JON W. DUDAS
*Director of the United States Patent and Trademark Office*